(12) United States Patent
Solar et al.

(10) Patent No.: US 7,588,581 B2
(45) Date of Patent: Sep. 15, 2009

(54) PLACEMENT OF CHRONIC MICRO-CATHETER DEVICE AND METHOD

(75) Inventors: Matthew S. Solar, Indialantic, FL (US); Kari Parmer, Melbourne, FL (US); David Lee, Melbourne Beach, FL (US); Frank Murdock, Indialantic, FL (US)

(73) Assignee: Medtronic, Inc., Minneapolis, MN (US)

( * ) Notice: Subject to any disclaimer, the term of this patent is extended or adjusted under 35 U.S.C. 154(b) by 1381 days.

(21) Appl. No.: 10/106,773

(22) Filed: Mar. 26, 2002

(65) Prior Publication Data

US 2003/0187459 A1    Oct. 2, 2003

(51) Int. Cl.
*A61F 11/00* (2006.01)
(52) U.S. Cl. .................. 606/129; 606/108; 604/164.05
(58) Field of Classification Search ................. 606/108, 606/129; 604/164.01–170.03, 264, 543, 604/541, 506, 272, 93.01; 600/434, 129, 600/114, 128–130
See application file for complete search history.

(56) References Cited

U.S. PATENT DOCUMENTS

| | | | |
|---|---|---|---|
| 3,347,224 A | 10/1967 | Adams | |
| 3,631,848 A | 1/1972 | Muller | |
| 3,665,916 A | 5/1972 | Kobayashi et al. | |
| 3,754,555 A | 8/1973 | Schmitt | |
| 3,996,939 A | 12/1976 | Sheridan et al. | 128/351 |
| 4,136,701 A | 1/1979 | Barton et al. | |
| 4,306,562 A * | 12/1981 | Osborne | 604/523 |
| 4,357,496 A | 11/1982 | Dutcher et al. | |
| 4,522,212 A | 6/1985 | Gelinas et al. | |
| 4,548,597 A | 10/1985 | Nelson | 604/43 |
| 4,637,388 A | 1/1987 | Melendy | 127/207.14 |
| 4,666,438 A * | 5/1987 | Raulerson | 604/272 |
| 4,668,221 A * | 5/1987 | Luther | 604/164.03 |
| 4,692,147 A | 9/1987 | Duggan | |
| 4,846,791 A | 7/1989 | Hattler et al. | 604/43 |
| 5,113,859 A | 5/1992 | Funke | |
| 5,221,255 A | 6/1993 | Mahurkar et al. | 604/43 |
| 5,236,424 A | 8/1993 | Imran | |
| 5,237,996 A | 8/1993 | Waldman et al. | 128/642 |

(Continued)

FOREIGN PATENT DOCUMENTS

EP    0479435    4/1992

(Continued)

OTHER PUBLICATIONS

T. Riechert and H. Spuler, "Instrumentation of Stereotaxy," Stereotaxy of the Human Brain, 1982, pp. 350-363.

*Primary Examiner*—Nicholas D Lucchesi
*Assistant Examiner*—Theodore J Stigell
(74) *Attorney, Agent, or Firm*—Harness Dickey & Pierce, PLC

(57) ABSTRACT

A device and method of placement of a chronic micro-catheter is shown that allows effective guiding of micro-catheters through a host catheter that is later removable while leaving the micro-catheter implanted in place within the patient. The novel configuration allows the micro-catheter to be completely radially enclosed during insertion, and still allows the host catheter to be removed, leaving the micro-catheter behind. Additionally, the configuration allows several micro-catheters to be placed at any number of depths and orientations while still using a minimally invasive host catheter.

21 Claims, 9 Drawing Sheets

U.S. PATENT DOCUMENTS

| | | | |
|---|---|---|---|
| 5,259,387 A | 11/1993 | dePinto | |
| 5,282,845 A | 2/1994 | Bush et al. | |
| 5,312,355 A * | 5/1994 | Lee | 604/160 |
| 5,314,462 A | 5/1994 | Heil, Jr. et al. | |
| 5,327,889 A | 7/1994 | Imran | 128/642 |
| 5,342,295 A | 8/1994 | Imran | |
| 5,476,498 A | 12/1995 | Ayers | |
| 5,514,174 A | 5/1996 | Heil, Jr. et al. | |
| 5,551,426 A | 9/1996 | Hummel et al. | |
| 5,609,623 A | 3/1997 | Lindegren | |
| 5,685,839 A | 11/1997 | Edwards et al. | |
| 5,711,316 A | 1/1998 | Elsberry et al. | |
| 5,713,922 A | 2/1998 | King | |
| 5,722,402 A | 3/1998 | Swanson et al. | |
| 5,725,525 A | 3/1998 | Kordis | |
| 5,755,693 A * | 5/1998 | Walker et al. | 604/160 |
| 5,792,186 A | 8/1998 | Rise | |
| 5,817,034 A * | 10/1998 | Milliman et al. | 600/566 |
| 5,925,070 A | 7/1999 | King et al. | |
| 5,964,796 A | 10/1999 | Imran | 607/122 |
| 6,038,472 A | 3/2000 | Williams et al. | |
| 6,080,174 A * | 6/2000 | Dubrul et al. | 606/185 |
| 6,094,596 A | 7/2000 | Morgan | |
| 6,094,598 A | 7/2000 | Elsberry et al. | |
| 6,126,631 A | 10/2000 | Loggie | 604/43 |
| 6,129,685 A | 10/2000 | Howard, III | |
| 6,142,926 A | 11/2000 | Schneiderman | 600/3 |
| 6,179,813 B1 * | 1/2001 | Ballow et al. | 604/164.01 |
| 6,385,472 B1 | 5/2002 | Hall et al. | |
| 6,520,951 B1 * | 2/2003 | Carrillo et al. | 604/516 |
| 6,837,873 B1 * | 1/2005 | Polley et al. | 604/164.01 |
| 2002/0065486 A1 * | 5/2002 | Balbierz et al. | 604/164.02 |
| 2004/0167478 A1 * | 8/2004 | Mooney et al. | 604/264 |
| 2005/0131399 A1 * | 6/2005 | Loeb et al. | 606/15 |
| 2005/0166924 A1 * | 8/2005 | Thomas et al. | 128/207.14 |

FOREIGN PATENT DOCUMENTS

| | | |
|---|---|---|
| EP | 0965359 | 12/1999 |
| WO | 95/19804 | 7/1995 |
| WO | 96/10961 | 4/1996 |
| WO | 97/39797 | 10/1997 |
| WO | 98/48887 | 11/1998 |
| WO | 99/00067 | 1/1999 |

\* cited by examiner

PLACEMENT OF CHRONIC MICRO-CATHETER DEVICE AND METHOD

BACKGROUND

1. Field of the Invention

This invention relates to medical devices. Specifically, but not by way of limitation, this invention relates to inserting a micro-catheter such as an electrode into a patient.

2. Background

In this document, any medical device that acts on the tissue of the patient is classified as a primary medical device. Other medical devices that assist in the positioning or handling or operation of the primary medical device are called secondary medical devices. While the secondary medical device could be used to introduce a primary medical device to several locations within a patient, for the discussion in this document, a neurosurgical procedure will be used as an example.

A common surgical technique inserts primary medical devices into patients through small openings that are surgically cut in the patient. One category of medical devices that can be inserted into a patient is catheters, which is a broad term, and could include several devices. One such catheter includes a drug delivery device using a hollow passage in the catheter to pump a drug to a selected location in the patient. Another catheter includes ablation technology where lasers are used to remove tissue. Another catheter includes an electrical contact that delivers an electrical signal to a point of interest inside a patient. While the above listed devices could all be considered catheters, the list is not exhaustive. Any of a number of other devices could be inserted inside a patient in such a way as to be classified as a catheter.

In this document, references to coordinates with respect to catheters will refer to axial locations and radial locations. Longitudinal or axial locations are locations along an insertion axis of a catheter. Radial locations will use the conventional 2-dimensional radial coordinates (r, θ) in a circle that is normal to the insertion axis. By combining an axial coordinate with the radial coordinates, a point can be located in three dimensional space relative to a given reference frame, such as the patient. Descriptions of the insertion axis in this document will generally refer to depth inside a patient along a line. It should be noted that although catheters are generally not inserted along a straight line, a generally linear depth model will be used for ease of discussion. Also, the axial end, or tip of the catheter that is inserted into a patient is referred to herein as the distal end of the catheter, while the axial end of the catheter that remains toward the outside the patient is referred to as the proximal end.

In one method of inserting a primary catheter, a secondary catheter is used to guide the primary catheter to the target location within the patient. In this configuration, the primary catheter is referred to as a micro-catheter, and the secondary catheter is referred to as a host catheter. Smaller catheters are desirably less invasive to the patient. In one type of surgical procedure, several micro-catheters are inserted in the same small opening in the patient at one time. However, the micro-catheters frequently lack the structural rigidity to be accurately inserted into the patient. The host catheter provides such rigidity. The micro-catheter and host catheter configuration is convenient because is allows more precise insertion of the more delicate micro-catheters.

A problem associated with the micro-catheter and host catheter configuration is that when several micro-catheters need to be inserted through a small incision, there is limited space available for insertion. The host catheter is typically of a large diameter that is similar in size to the diameter of the incision. There is not adequate room for several host catheters to each insert one micro-catheter.

One prior approach to this problem has been to insert multiple micro-catheters along a single host catheter. As shown in FIG. 1, a micro-catheter 150 can be inserted through one of multiple lumens 122 in a host catheter 100, and directed from a proximal end 120 of the host catheter 100 to various exiting openings 112 at a distal tip 110 of the host catheter 100. In this way, several micro-catheters can be inserted through an incision, thereby keeping the procedure less invasive. The example shown in FIG. 1 also allows a choice of several radial directions for the micro-catheter 150, depending on which lumen 122 of the host catheter 100 is chosen for insertion.

A limitation of this approach is that when using a single host catheter to implant multiple micro-catheters, all the micro-catheters must be implanted at the same depth inside the incision. Additionally, only one micro-catheter can be implanted in each radial direction, because each directional channel only accommodates one micro-catheter.

One approach to avoiding this limitation has been to further increase the number of channels in the host catheter, and to have the channels exit the host catheter at various depths and radial directions along the host catheter. In this way, by choosing an appropriate channel in the host catheter, each micro-catheter can be implanted at varying depths or radial orientations. However, this approach necessarily involves a larger, more invasive, host catheter, and the choices of depth locations and radial directions for the micro-catheters is limited by the predetermined exit locations of channels in the host catheter.

What is needed is a device and method to implant several micro-catheters at varying depths with a larger range of positioning options that does not require a larger, more invasive host catheter.

Another problem with the previous listed approaches occurs when using another type of procedure, where it is desirable to leave the micro-catheters implanted in the patient for extended periods of time, up to several days or weeks. A micro-catheter that is left implanted in a patient for extended periods of time is referred to as a "chronic" micro-catheter. In this type of procedure it is impractical to leave the host catheter inserted in the patient, because it is bulky, and extends a substantial distance outside the patient, and may be accidentally bumped over the extended time period. There is also an increased risk of infection with the larger opening being exposed for an extended time period. It is difficult or impossible to remove the host catheter of the previous examples and leave the micro-catheters implanted in their locations.

As further shown in FIG. 1, the distal tips of catheters, such as the distal tip 160 of micro-catheter 150, are small and typically have a diameter that is similar to a diameter along the axial length of the catheter. However, the proximal tips of catheters often have large fittings attached to them that are used for coupling to external, secondary medical devices. In FIG. 1, micro-catheter 150 is shown with a fitting 172 located at its proximal end 170. The fittings 172 are typically permanently attached to the micro-catheters 150. Micro-catheters are typically inserted into a close tolerance, enclosed longitudinal channel to guide them to the target location. The problem associated with removing the host catheter and leaving behind the micro-catheter is that the close tolerance, longitudinal channel will not fit over the much larger fitting 172 on the proximal tip of the micro-catheter. Because existing devices require axial removal of the host catheter, if the host catheter is to be removed, the micro-catheter must also be removed.

What is needed is a host catheter that can be removed while allowing the micro-catheter to remain implanted at its target location inside the patient.

SUMMARY OF THE INVENTION

The invention includes a guide device with a guide axis is shown that includes a sheath that defines a radially enclosed longitudinal cavity in a first state. The sheath may be split substantially along a longitudinal wall and radially removed from the guide axis in a second state. The guide device also includes a mandrel that, when inserted into the sheath in its first state, defines a substantially continuous longitudinal guide region bounded on a first longitudinal portion by the mandrel, and on a second longitudinal portion by the sheath.

The guide device may also define a plurality of longitudinal guide regions. The mandrel may include a shield portion on a distal end of the mandrel. The shield portion may be changeable between a first state and a second state. There may also be a ramp located at the distal end of the mandrel that directs the guide region outward with a radial component from the guide axis.

In another embodiment, the guide device includes a sheath that defines an enclosed longitudinal cavity in a first state, and may be split substantially along a longitudinal wall and radially removed from the guide axis in a second state. The second embodiment also includes a first mandrel that, when inserted in the sheath in its first state, provides structural support to the sheath during insertion. The first mandrel has a shield portion attached to a distal end portion that substantially shields a distal opening in the sheath in its first state. The second embodiment also includes a second mandrel that may be inserted in the sheath in place of the first mandrel such that the second mandrel defines a substantially continuous longitudinal guide region bounded on a first longitudinal portion by the semi-rigid mandrel, and on a second longitudinal portion by the sheath.

Although specific embodiments have been illustrated and described herein, it will be appreciated by those skilled in the art that any arrangement which is calculated to achieve the same purpose may be substituted for the specific embodiment shown. This document is intended to cover any adaptations or variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

DETAILED DESCRIPTION

Figure 1:
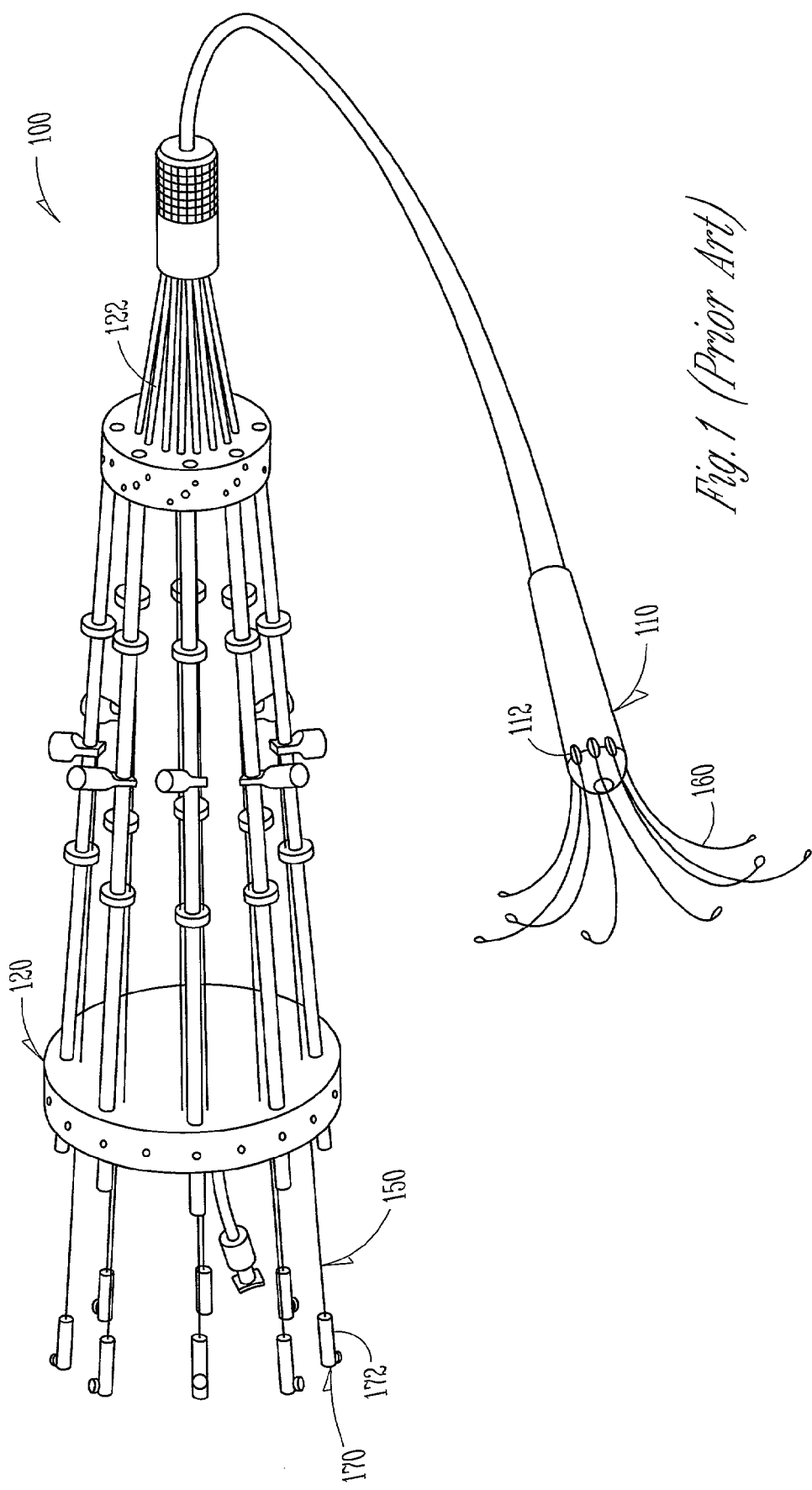
FIG. 1 is a perspective view of a multiple lumen host catheter and a micro-catheter.
Figure 2:
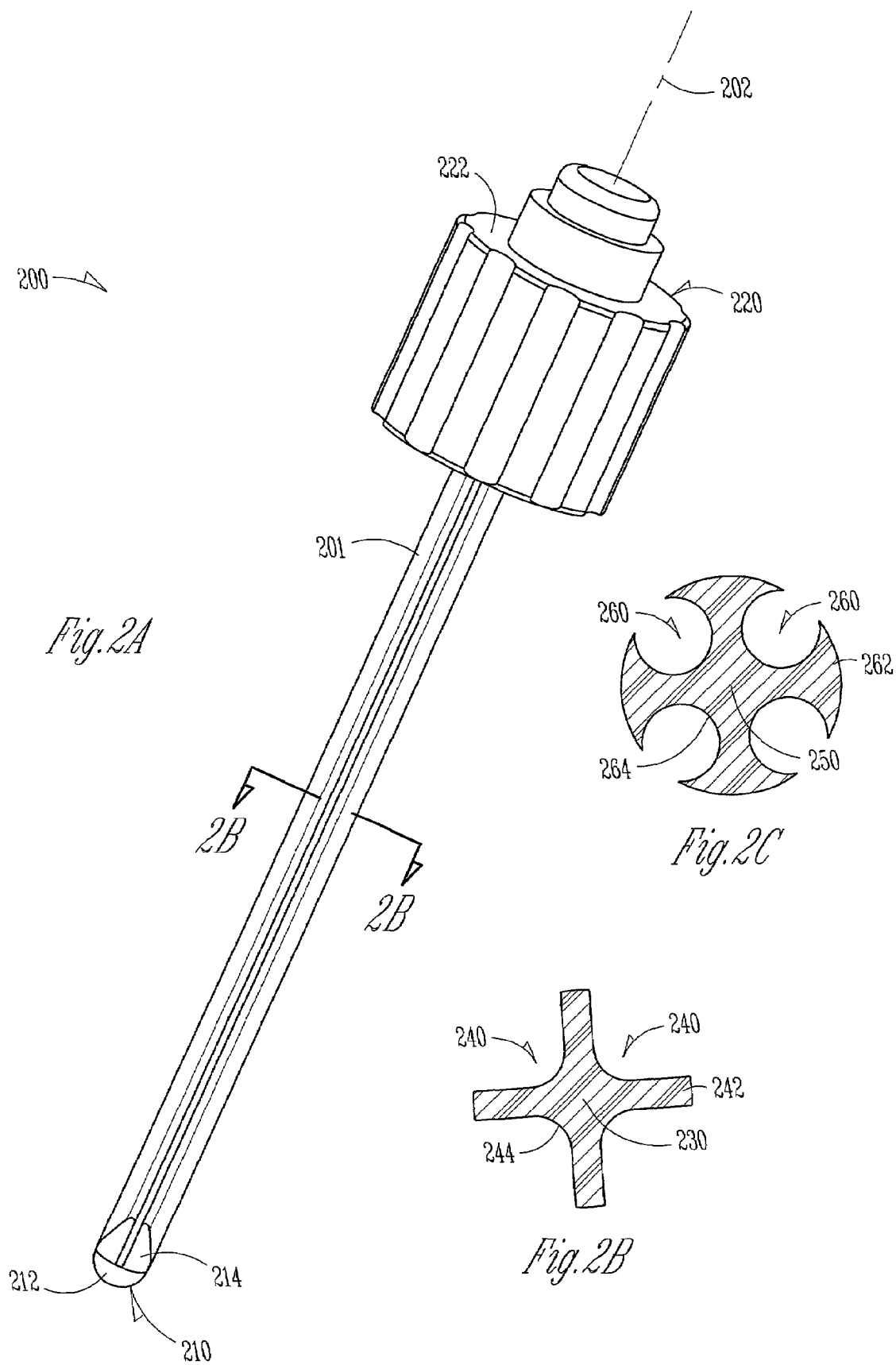
FIG. 2a is a perspective view of a mandrel in an embodiment of the invention.
FIG. 2b is a section view along line 2b-2b.
FIG. 2c is a cross section of a mandrel in an embodiment of the invention.

FIG. 2a shows a mandrel 200 including a mandrel shaft 201, and a knob 222. The mandrel 200 has a distal end 210 and a proximal end 220. The distal end 210 is inserted into the patient, while the proximal end 220 is used to insert a primary medical device during the procedure. The proximal end 220 of the mandrel 200 includes the knob 222 which is used to handle and adjust the mandrel 200 during the procedure. The knob 222 may also include adaptations that accept a fitting from a secondary medical device. The mandrel 200 in this embodiment has a straight central axis 202. Other embodiments of the mandrel 200 include curved shaft mandrels. Curved shafts can assist in directional placement of micro-catheters.

FIG. 2b shows a sectional view of the shaft 201 of the mandrel 200 from FIG. 2a. The cross section in this embodiment includes an axial portion 230 that is located along the central axis 202 of the mandrel 200. Four channel portions 240 are created by four divider portions 242. Located at the intersection of the divider portions 242, are beveled portions 244. Although four channel portions 240 are included in this embodiment, either a single channel portion, or several channel portions could be used without departing from the scope of the invention. Although the axial portion 230 in this embodiment is concentric with the central axis 202, other embodiments may include an axial portion 230 that is located on the periphery of the mandrel 200.

At the distal end 210 of the mandrel 200 in FIG. 2a, there is a shield portion 212. The shield portion 212 in this embodiment is rounded to avoid damaging tissue during insertion. Just above the shield portion 212, there is a number of ramps 214. Each ramp is located in one of the channel portions 240, the ramps 214 directing the distal end of the channel portions 240 outward with a radial component from the central axis 202 of the mandrel 200.

FIG. 2c shows another embodiment of a cross section of the mandrel 200. An axial portion 250 is shown, with divider portions 262. The divider portions 262 define a number of channel portions 260. In this embodiment, the channel portions 260 each contain a contact surface 264 that outlines a portion of a circle. In this embodiment, the contact surfaces 264 are designed to match a radius of a micro-catheter.

Figure 3:
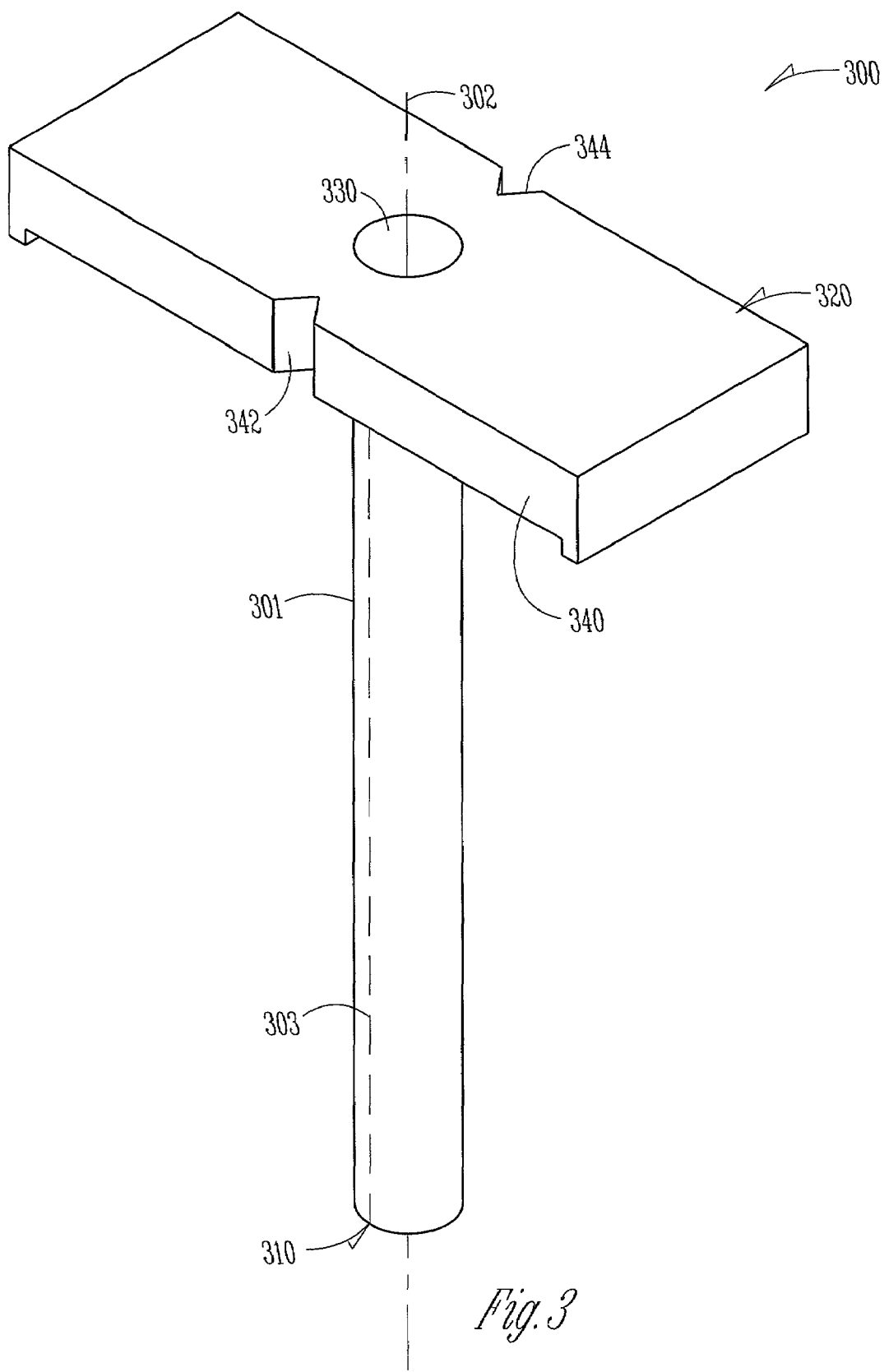
FIG. 3 is a perspective view of a sheath in an embodiment of the invention.

FIG. 3 shows a peel-away sheath 300 in a first state. The sheath 300 includes a tube 301, and a handle 340. The sheath 300 has a distal end 310 and a proximal end 320, and a central axis 302. There is a longitudinal or axial opening 330 through the length of the sheath 300, passing along the tube 301. The opening 330 is large enough to accept the mandrel 200 from FIG. 2A. The handle 340 is attached to the proximal end of the sheath. In this example, the handle includes a first notch 342 adjacent to the central axis 302, and a second notch 344 opposite the first notch an also adjacent to the central axis 302. In this embodiment, along the tube 301 is a first linear weakened portion 303. The weakened portion aligns with the first notch 342. Also included on the tube 301 is a second weakened portion (not shown) that aligns with the second notch 344. The notches 342 and 344 along with the weakened portions, allow the peel-away sheath 300 to be split apart radially during the procedure for removal of the sheath.

Figure 4:
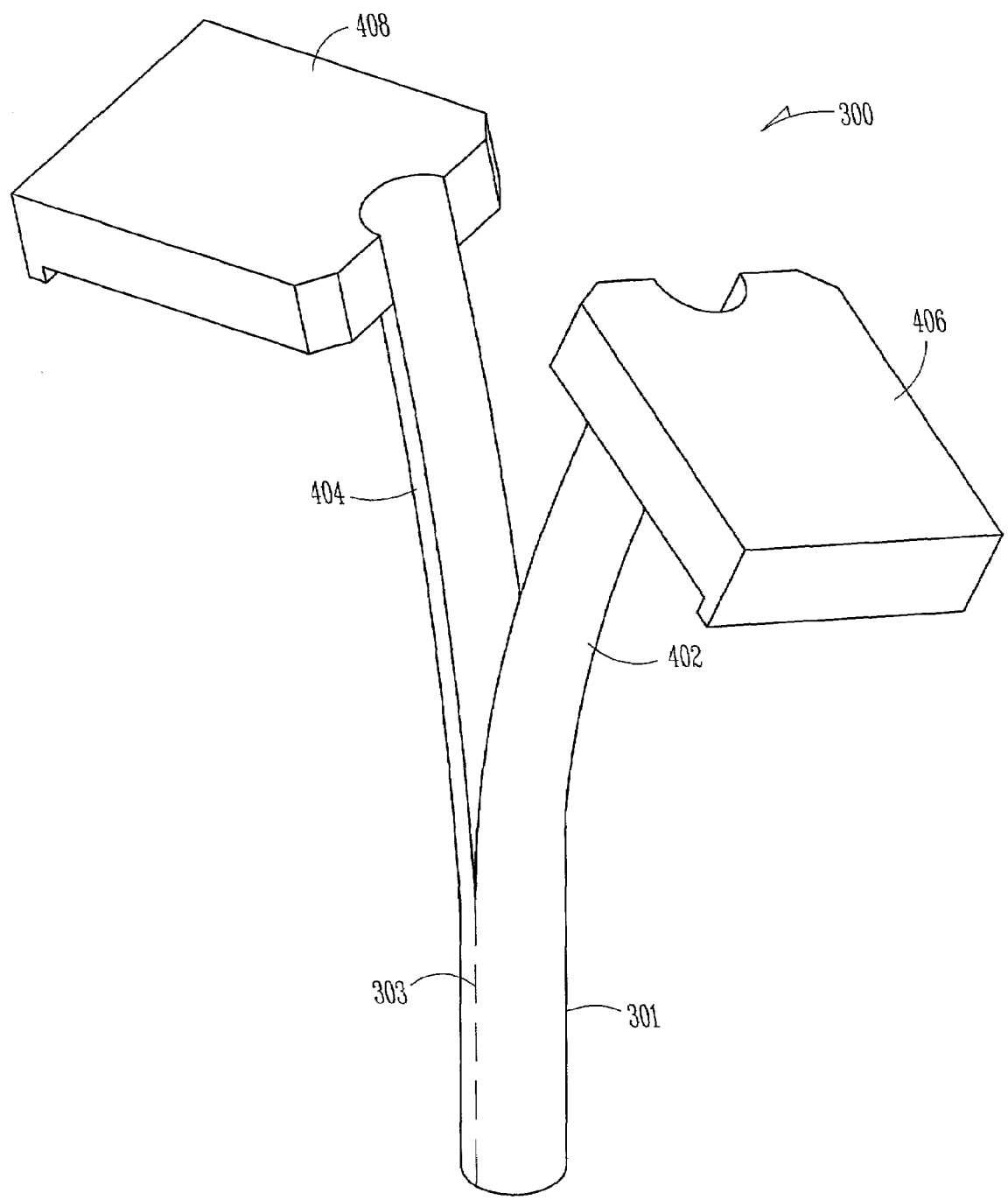
FIG. 4 is a perspective view of the sheath in another embodiment of the invention.

FIG. 4 shows the peel-away sheath in transition to a second state. The second state is obtained by splitting the sheath 300 for removal from the patient. The handle 320 splits into a first handle portion 406 and a second handle portion 408. The sheath also splits into a first longitudinal portion 402 and a second longitudinal portion 404. The split of the handle 320 in this embodiment occurs at the first and second notch 342, 344 shown in FIG. 3, and the tube 301 is split along the weakened portions as shown in FIG. 4.

Figure 5:
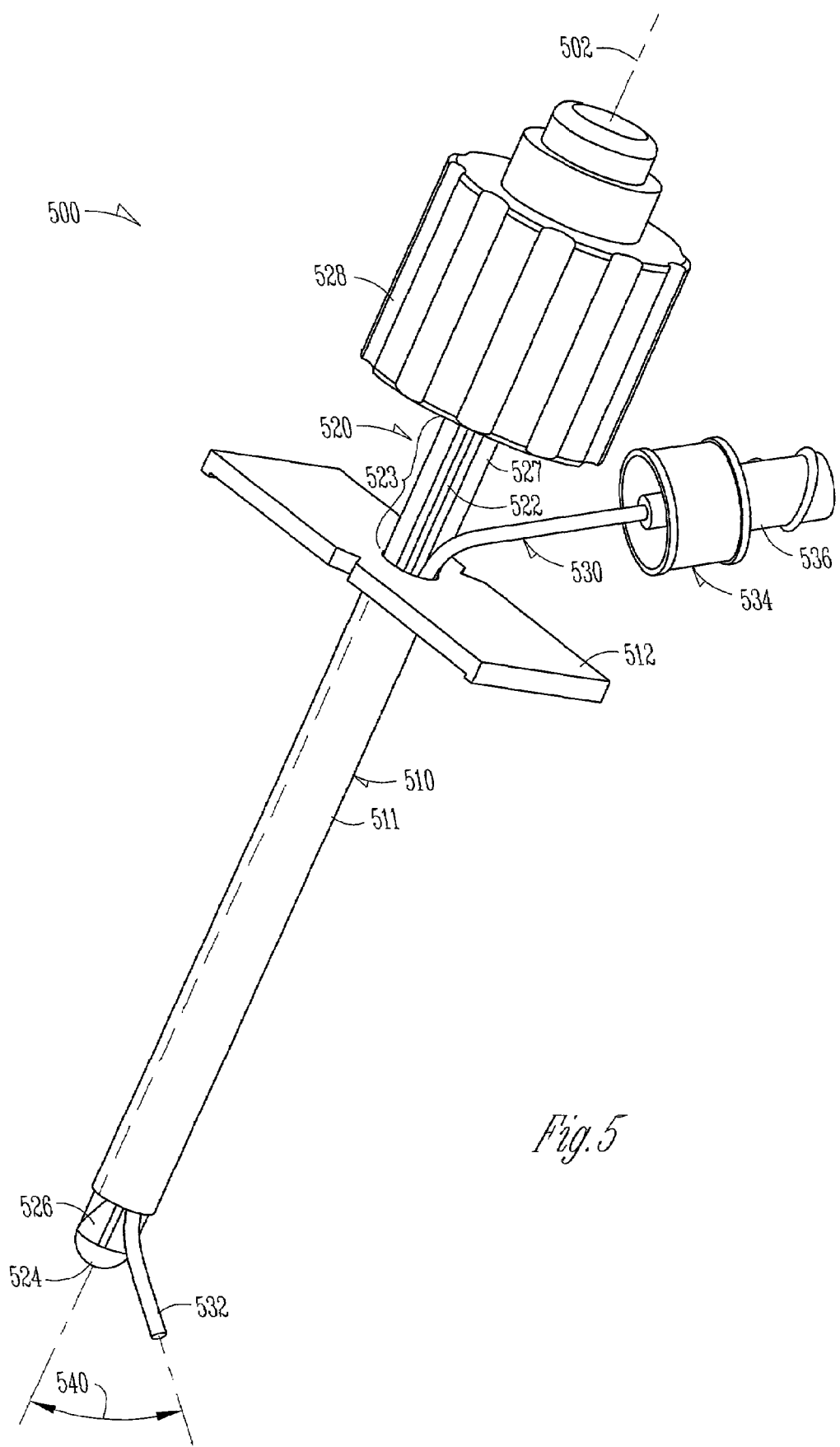
FIG. 5 is a perspective view of an introduction system in an embodiment of the invention.

FIG. 5 shows an insertion system. The system includes a host catheter 500, the host catheter being formed from a mandrel 520, and a peel-away sheath 510. The mandrel 520 includes a number of channels 522 that travel along a shaft 527 of the mandrel 520. At the distal tip of the mandrel 520 are a shield portion 524 and a number of ramps 526 as shown in FIG. 2a-2b above. The system also includes a micro-catheter 530 that is inserted through the host catheter 500. The micro-catheter has a distal end 532 and a proximal end 534 with a fitting 536 attached at the proximal end.

In operation, the mandrel 520 is first inserted into the peel-away sheath 510 such that the shield portion 524 extends only far enough past the distal end of the sheath to protect the distal opening of the sheath. This positioning of the depth of the mandrel 520 in the sheath 510 can be accomplished by adjusting the knob 528 to a desired position along the axis 502 of the mandrel. The position of the knob 528 can be fixed such that when the knob 528 butts against the handle 512 of the sheath 510, the shield portion 524 does not extend too far beyond the distal tip of the sheath 510.

After the mandrel has been positioned in the sheath, the host catheter is inserted into the patient to a target location, such as a target location within the brain. The shield 524 protects the tissue in front of the distal end of the host catheter 500 from damage, allowing the host catheter 500 to be inserted to the target location with reduced trauma. After insertion, the knob 528 is then moved upwards away from the handle 512 of the sheath 510. The knob 528 is moved along the shaft 527 of the mandrel 520, while leaving the shaft 527 in its inserted position. After the knob 528 is re-positioned, the channels 522 in the mandrel are exposed and accessible from the side, or radial direction, of the mandrel. The shaft 527 is then inserted slightly further into the patient to expose the ramps 526 at the distal end of the host catheter 500.

The distal end 532 of the micro-catheter 530 is next inserted along one of the channels 522 in a radially exposed region 523 or side region of the mandrel 520. When the mandrel 520 is inserted into the sheath 510, the channels 522 of the mandrel divide the sheath into a number of enclosed passages that are bounded longitudinally on one portion by the mandrel 520, and on another portion by the sheath 510. The micro-catheter 530 then enters the enclosed passage that is defined by the particular channel 522 that it has been guided into. At the distal end of the host catheter 500, the micro-catheter is directed radially outward at an angle 540 by the ramp 526 that is associated with its channel 522 and enclosed passage. The micro-catheter exits the host catheter through the small opening between the shield portion 524 and the distal end of the sheath. The outward direction of the micro-catheter can therefore be chosen by selecting from various channel options in this embodiment.

Next, the host catheter 500 may be removed from the patient, leaving the micro-catheter 530 in place. In a first method, the mandrel 520 is removed first. Before removal of any component, the sheath 510 is peeled back as shown in FIG. 4 up to an insertion point in the patient. The micro-catheter 530 is held in place near the insertion point in the patient, and the mandrel 520 is then pulled axially back and out of the patient. Because the shield portion 524 and the ramp 526 do not contain a radial channel clearance for the micro-catheter 530, in this embodiment, when extracting the mandrel 520 first, the sheath 510 is slightly flexible. This allows the sheath 510 to expand radially to allow the shield portion 524 and the ramps 526 to pull through the sheath along side the micro-catheter 530. Alternatively, the mandrel 520 may fit loosely in the sheath 510 and the extra radial room from the loose fit will allow the shield portion 524 and the ramps 526 to pull through the sheath along side the micro-catheter. Because the channels 522 in the mandrel 520 are radially accessible, the mandrel 520 pulls free of the micro-catheter once it clears the sheath 510. After the mandrel 520 is removed, in this method, the sheath is removed last by pulling back axially, and peeling the sheath apart radially as it exits the insertion point. The micro-catheter 530 remains in place, with the host catheter 500 completely removed radially from the micro-catheter 530.

Alternative to removing the mandrel first, using a second method, the sheath may be removed first. Again, the sheath 510 is peeled back as shown in FIG. 4 up to an insertion point in the patient, and the micro-catheter 530 is held in place near the insertion point in the patient. The sheath 510 is then removed by pulling back axially, and peeling the sheath apart radially as it exits the insertion point. Once the sheath 510 has been removed, the mandrel may be pulled back axially and removed. Similar to the first method, because the channels in the mandrel 520 are radially accessible, the mandrel 520 pulls free of the micro-catheter once it clears the insertion point. Using this second method, the micro-catheter 530 again remains in place, with the host catheter 500 completely removed radially from the micro-catheter 530.

With this two component mandrel/sheath configuration, there are several advantages. The guiding of the micro-catheters is highly effective due to the radially enclosed nature of the passages. Guiding of the micro-catheters is more effective using completely radially enclosed passages, than using passages that are only partially radially enclosed. Using two components also gives the possibility of using two different materials. The sheath material may be comprised of a low friction material, while the mandrel may be comprised of a more rigid material to aid in insertion. The mandrel may also include an angled or bent configuration that is separate from the sheath to better direct the micro-catheter to an angled position. This two part configuration allows the micro-catheter to be completely radially enclosed during insertion, and still allows the host catheter to be removed, leaving the micro-catheter behind. Additionally, a first host catheter/micro-catheter can be implanted at any number of depths and radial directions, then the first host catheter can be removed and a second host catheter/micro-catheter can be implanted at any chosen second depth and radial direction. By repeatedly using this procedure, a large number of micro-catheters can be placed inside a patient at an increased number of positions, without increasing the diameter of the host catheter. The procedure remains minimally invasive, and the micro-catheters that are inserted may all be left behind after removing the host catheters.

Figures 6A, 6B:
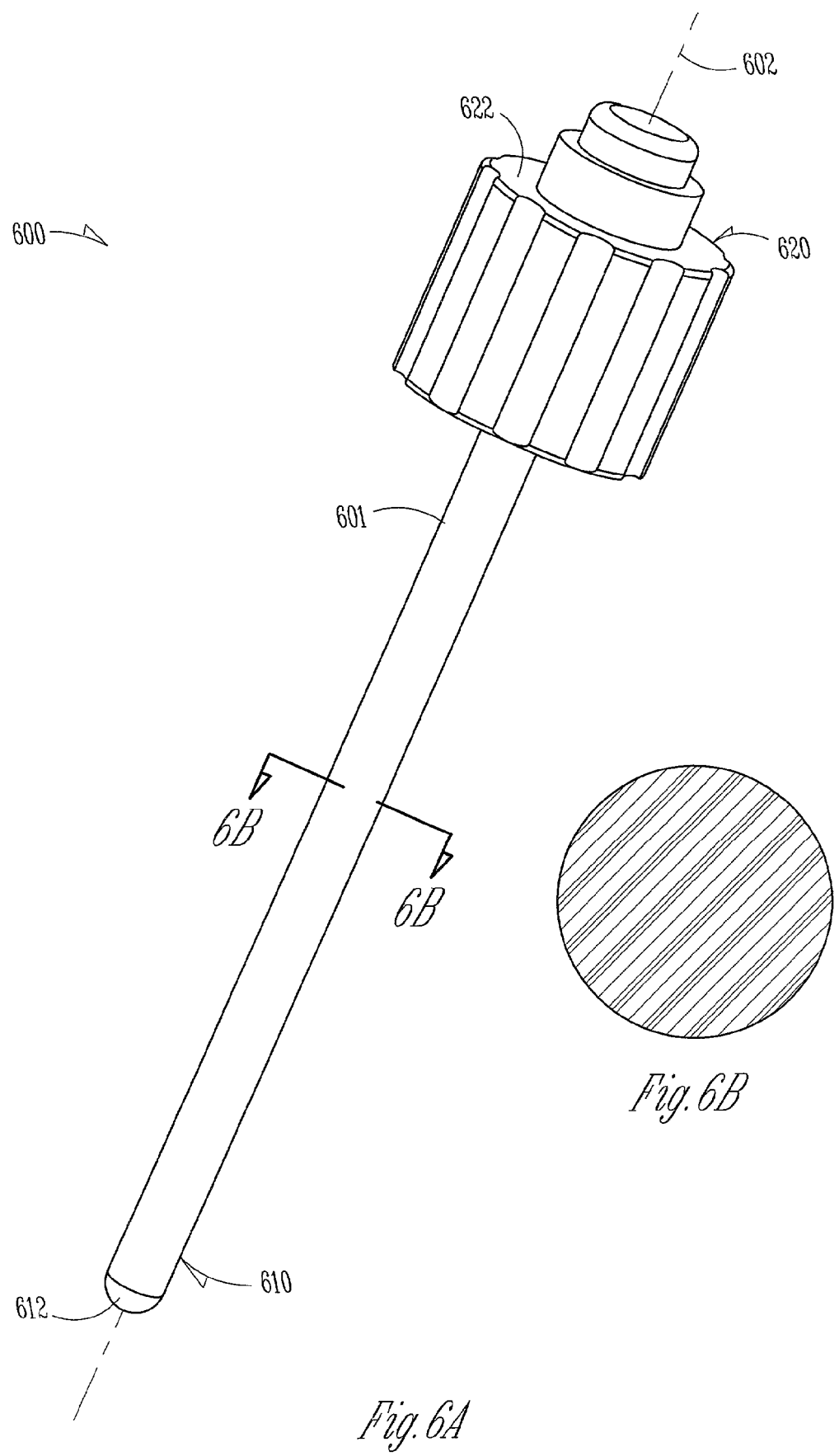
FIG. 6a is a perspective view of a mandrel in an embodiment of the invention.
FIG. 6b is a section view along line 6b-6b.

Another embodiment of the invention is shown in FIGS. 6a, 6b and 7a, 7b. The host catheter in this embodiment uses a single peel-away sheath as shown in FIGS. 3 and 4, and two different mandrels. The first mandrel 600 is shown in FIG. 6a. It includes a first shaft 601 and a first knob 622. The knob 622 is attached at a proximal end 620 of the first mandrel 600, and a rounded shield portion 612 is included at a distal end 610 of the first shaft 601. As shown in FIG. 6b, the cross section of the first mandrel is solid round.

Figures 7A, 7B:
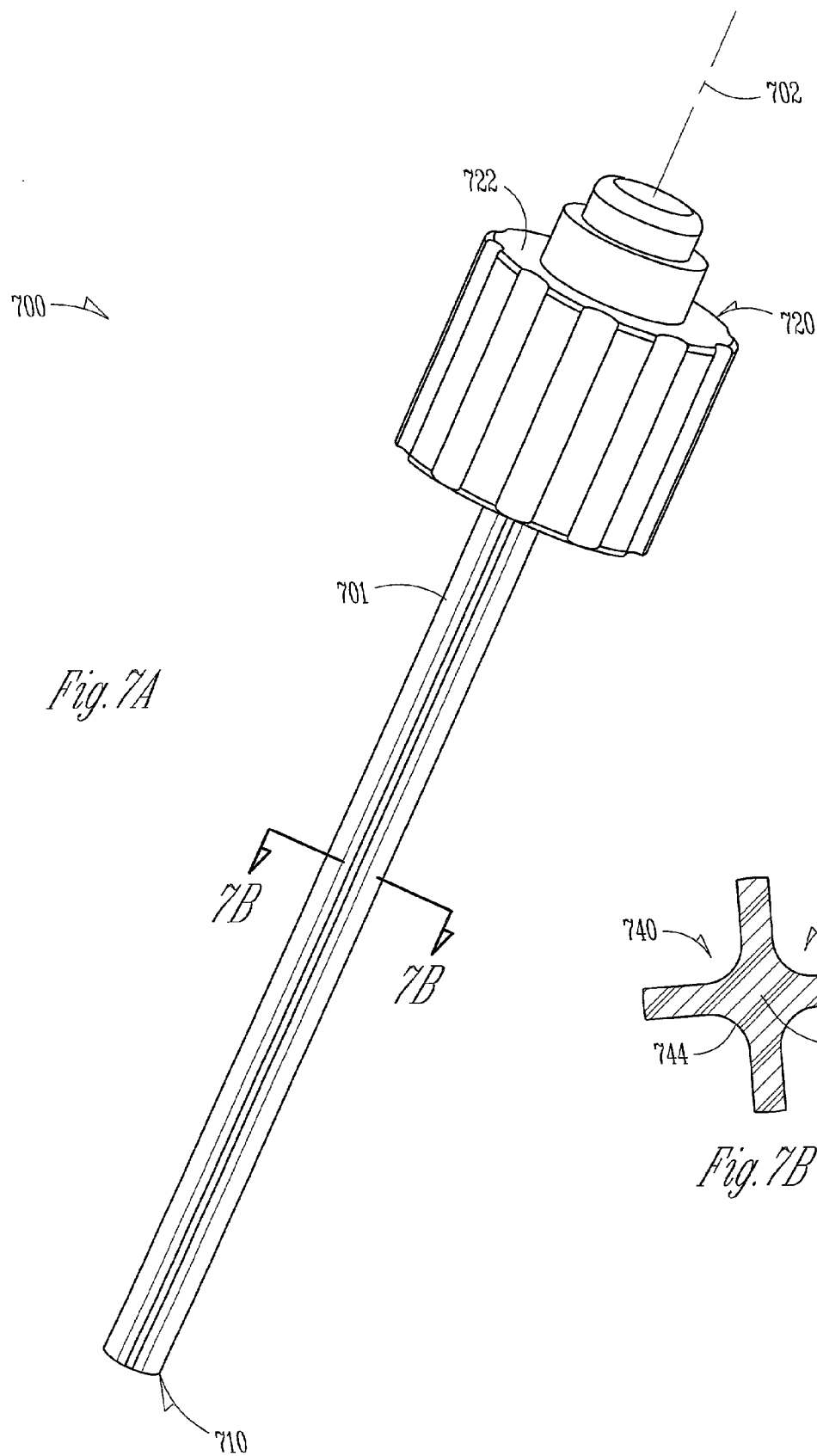
FIG. 7a is a perspective view of a mandrel in an embodiment of the invention.
FIG. 7b is a section view along line 7b-7b.

A second mandrel 700 is shown in FIG. 7a. It includes a second shaft 701 with a distal end 710, and a second knob 722. The second knob 722 is attached at a proximal end 720 of the second mandrel 700. FIG. 7b shows a sectional view of the shaft 701 of the second mandrel 700 from FIG. 7a. The cross section in this embodiment includes an axial portion 730 that is located along the central axis 702 of the second mandrel 700. Four channel portions 740 are created by four divider portions 742. Located at the intersection of the divider portions 742, are beveled portions 744. Although four channel portions 740 are included in this embodiment, either a single channel portion, or several channel portions could be used without departing from the scope of the invention. Although the axial portion 730 in this embodiment is concentric with the central axis 702, other embodiments may include an axial portion 730 that is located on the periphery of the second mandrel 700.

In operation, the first and second mandrels 600 and 700 are used with the sheath 300 shown in FIGS. 3 and 4. The first mandrel 600 is first inserted into the peel-away sheath 300 such that the shield portion 612 extends only far enough past the distal end 310 of the sheath to protect the distal opening of the sheath. This positioning of the depth of the first mandrel 600 in the sheath can be accomplished by adjusting the knob 622 to a desired position along an axis 602 of the first mandrel. The position of the knob 622 can be fixed such that when the knob 622 butts against the handle 340 of the sheath, the shield portion 612 does not extend too far beyond the distal tip 310 of the sheath.

After the first mandrel 600 has been positioned in the sheath, the host catheter is inserted into the patient to a target location, such as a target location within the brain. The shield 524 protects the tissue in front of the distal end of the host catheter 500 from damage, allowing the host catheter 500 to be inserted to the target location with reduced trauma. After insertion, the first mandrel 600 is removed and the second mandrel 700 is inserted in its place. Because the insertion step has already been performed using the blunt tipped first mandrel 600, the second mandrel does not need a shield portion for tissue protection. The second mandrel therefore does not include any shield portion on its distal end 710.

The second mandrel 700 is inserted such that the distal end 710 does not extend beyond the distal end of the sheath, thus protecting the surrounding tissue. The knob 722 is positioned along the second shaft 701 such that the channels 522 in the mandrel are exposed and accessible from the side, or radial direction of the mandrel.

The distal end of a micro-catheter is next inserted along one of the channels 740 in a radially exposed region or side region of the second mandrel 700. Similar to the previously described embodiment, when the second mandrel 700 is inserted into the sheath, the channels of the second mandrel divide the sheath into a number of enclosed passages that are bounded longitudinally on one portion by the second mandrel, and on another portion by the sheath. The micro-catheter then enters the enclosed passage that is defined by the particular channel that it has been guided into. The micro-catheter exits the host catheter through the distal end of the enclosed passage, which is axially exposed, and unobstructed by a shield portion or a ramp in this embodiment.

Next, the host catheter is optionally removed from the patient, leaving the micro-catheter in place. Either the second mandrel or the peel-away sheath may be removed first, similar to the previous embodiment above. In this embodiment, there is no need for the sheath to be slightly expandable or to design the fit of the second mandrel within the sheath with extra clearance room. Because this embodiment does not include a shield portion or ramps, there are no clearance issues during removal of the second mandrel.

Figures 8A, 8B:
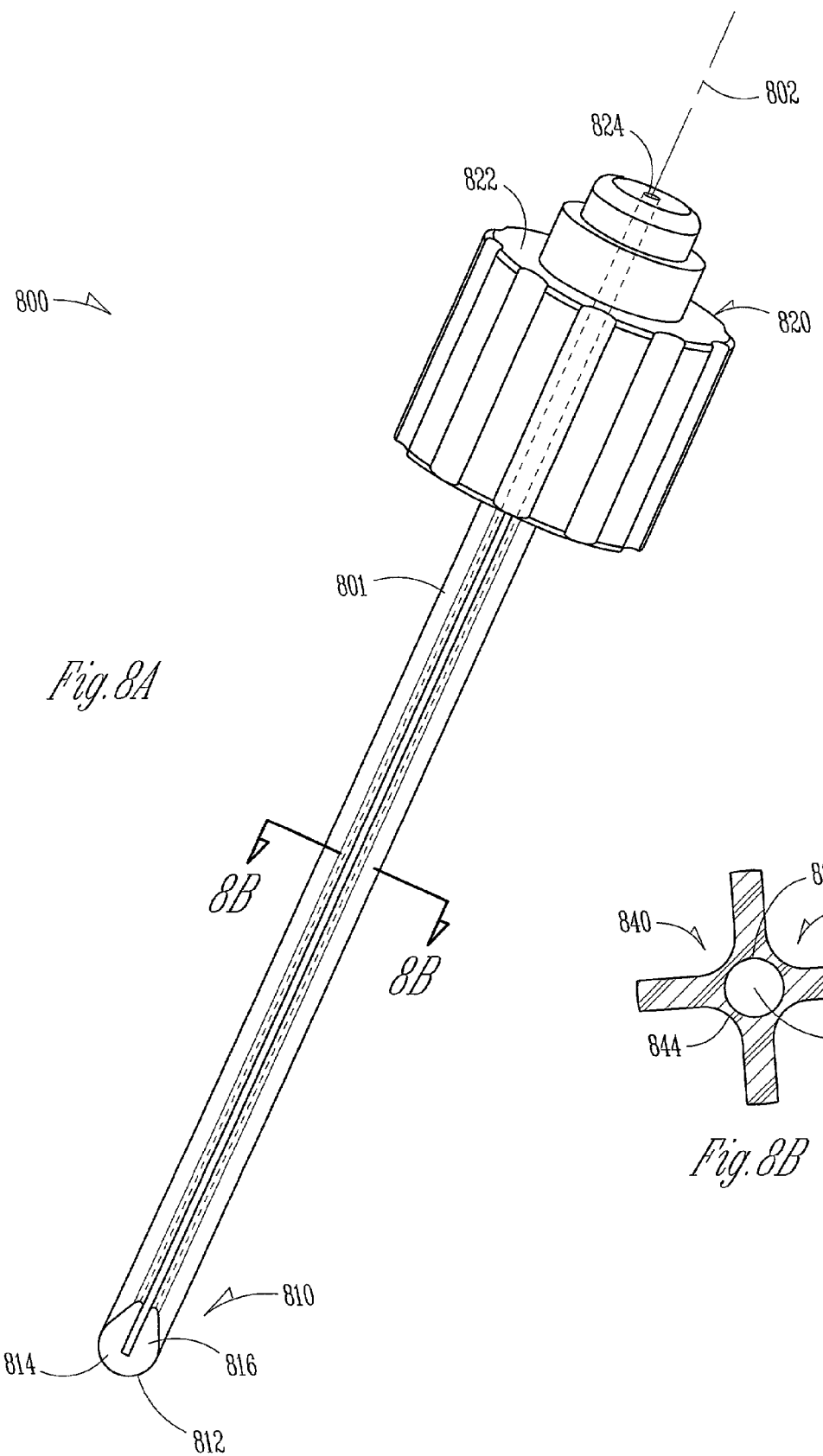
FIG. 8a is a perspective view of a mandrel in another embodiment of the invention in a first state of operation.
FIG. 8b is a section view along line 8b-8b.

FIG. 8a shows a further embodiment of the invention, including a mandrel 800, with a mandrel shaft 801, and a knob 822. The mandrel 800 has a distal end 810 and a proximal end 820. The distal end 810 is inserted into the patient, while the proximal end 820 is used to insert a primary medical device during the procedure. The proximal end 820 of the mandrel 800 includes the knob 822 which is used to handle and adjust the mandrel 800 during the procedure. The knob 822 may also include adaptations that accept a fitting from a secondary medical device. The mandrel 800 in this embodiment has a straight central axis 802. Other embodiments of the mandrel 800 include curved shaft mandrels. Curved shafts can assist in directional placement of micro-catheters. The mandrel 800 in one embodiment further includes a gas delivery passage 824. In one embodiment, the gas delivery passage 824 is substantially cylindrical, and runs longitudinally along the central axis 802.

FIG. 8b shows a sectional view of one shaft embodiment 801 from FIG. 8a. The cross section in this embodiment includes an axial portion 830 that is located along the central axis 802 of the mandrel 800. The gas delivery passage 824 is further illustrated in cross section. Four channel portions 840 are created by four divider portions 842. Located at the intersection of the divider portions 842, are beveled portions 844. Although four channel portions 840 are included in this embodiment, either a single channel portion, or several channel portions could be used without departing from the scope of the invention. Although the axial portion 830 in this embodiment is concentric with the central axis 802, other embodiments may include an axial portion 830 that is located on the periphery of the mandrel 800.

At the distal end 810 of the mandrel 800 in FIG. 8a, there is a dynamic shape changing portion 812. The dynamic shape changing portion 812 in this embodiment includes a shield portion 814 and a number of ramps 816. The shield portion 814 is rounded to avoid damaging tissue during insertion. Just above the shield portion 814, there is a number of ramps 816. Each ramp is located in one of the channel portions 840, the ramps 816 directing the distal end of the channel portions 840 outward with a radial component from the central axis 802 of the mandrel 800.

Figure 8C:
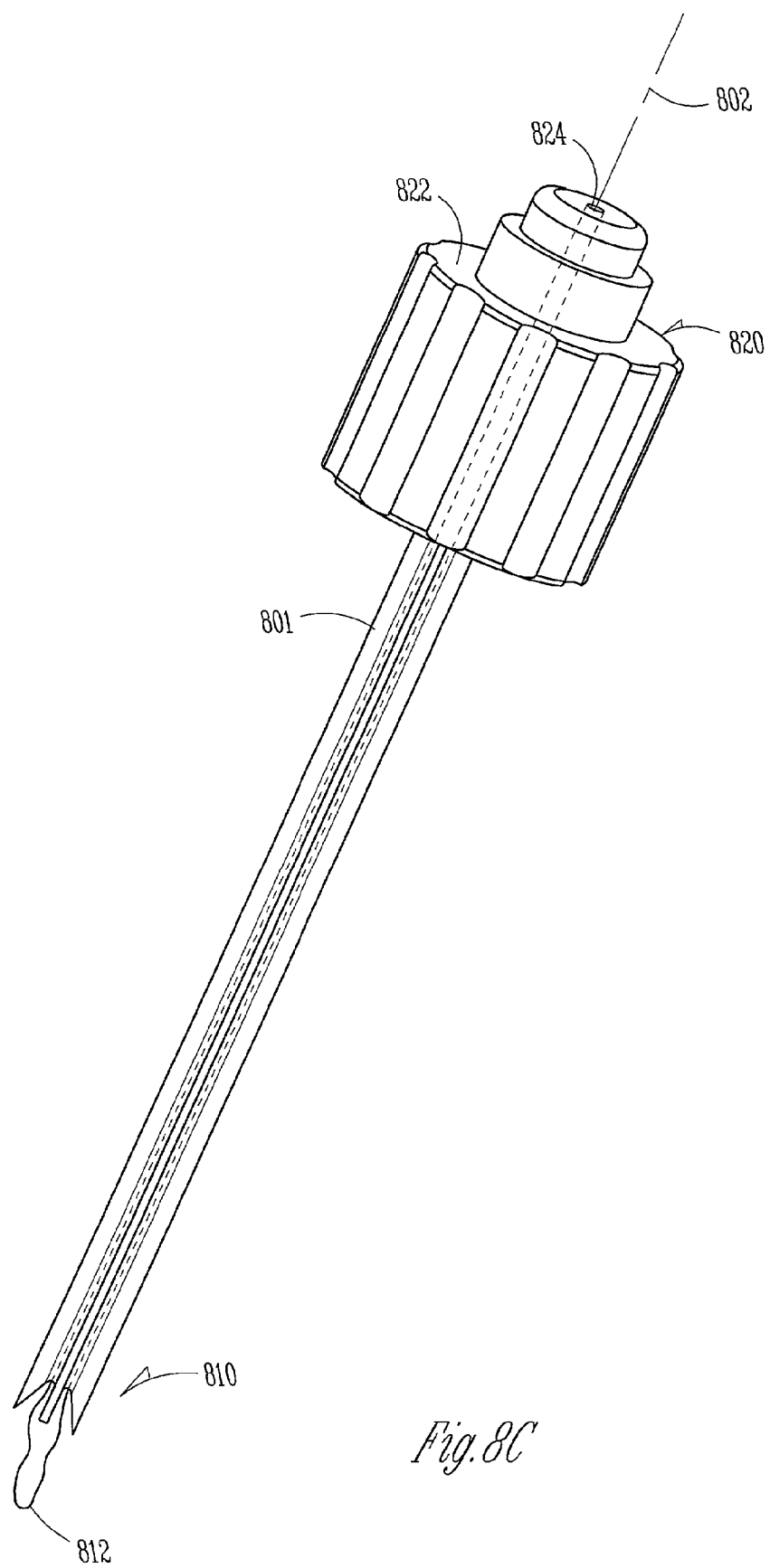
FIG. 8c is a perspective view of a mandrel in another embodiment of the invention in a second state of operation.

In one embodiment, the dynamic shape changing portion 812 includes an inflatable device, such as a balloon. The dynamic shape changing portion 812 in FIG. 8a is shown in an expanded first state. FIG. 8c shows the mandrel 800 with the dynamic shape changing portion 812 in a substantially collapsed second state. The first state of the dynamic shape changing portion 812 is used for directional insertion of a micro-catheter or similar device. The second state of the dynamic shape changing portion 812 is used for withdrawal of the mandrel 800 similar to methods described above. With the dynamic shape changing portion 812 in a deflated state, additional radial channel clearance is made available for the micro-catheter inside a sheath.

In operation, the dynamic shape changing portion 812 is placed in the first state by introducing a gas under pressure. In one embodiment, air is injected into the dynamic shape changing portion 812 to inflate it to the first state. In one embodiment, the gas is introduced or removed through the gas delivery passage 824. Using a supplementary device such as a syringe body is one acceptable method of channeling the gas to and from the dynamic shape changing portion 812.

CONCLUSION

Thus has been shown a device and method for placement of a chronic micro-catheter. A device and method has been shown that allows effective guiding of micro-catheters through a host catheter that is later removable while leaving the micro-catheter implanted in place within the patient. The novel configuration shown allows the micro-catheter to be completely radially enclosed during insertion, and still allows the host catheter to be removed, leaving the micro-catheter behind. Additionally, this configuration allows several micro-catheters to be placed at any number of depths and orientations while still using a minimally invasive host catheter.

Although specific embodiments have been illustrated and described herein, it will be appreciated by those skilled in the art that any arrangement which is calculated to achieve the same purpose may be substituted for the specific embodiment shown. This document is intended to cover any adaptations of variations of the present invention. It is to be understood that the above description is intended to be illustrative, and not restrictive. The scope of the invention includes any other applications in which the above structures and fabrication methods are used. The scope of the invention should be determined with reference to the appended claims, along with the full scope of equivalents to which such claims are entitled.

What is claimed is:

1. A guide device, having a guide axis, comprising:
  a sheath that defines a radially enclosed longitudinal cavity in a first state, and has a longitudinal weakened portion to allow the sheath to be split substantially along a longitudinal wall and radially removed from the guide axis in a second state;
  a mandrel, having an axial portion and a plurality of dividing members extending radially from the axial portion, the mandrel, when inserted into the sheath in its first state, defines a plurality of substantially continuous longitudinal guide regions, each guide region bounded by a longitudinal portion of the mandrel, and by a longitudinal portion of the sheath; and
  a shield portion on the mandrel, wherein when the mandrel is fully inserted in the sheath, the shield portion substantially shields a distal opening in the sheath in its first state.

2. The guide device of claim 1, wherein the axial portion is coaxial with the mandrel and the sheath when the mandrel is inserted in the sheath in its first state.

3. The guide device of claim 1, wherein the shield portion includes a dynamic shape changing portion.

4. The guide device of claim 1, wherein the shield portion includes a curved end portion.

5. The guide device of claim 1, further including a ramp located at a distal end of the guide region the ramp directing the distal end of the guide region at least partially radially outward from the guide axis.

6. The guide device of claim 5, further comprising:
  a primary medical device capable of insertion through the guide region.

7. The guide device of claim 5, wherein the shield portion is located at a distal end of the mandrel and substantially covers the distal opening of the sheath in the first state when the mandrel is fully inserted in the sheath.

8. The guide device of claim 1, wherein the mandrel is fully inserted into the sheath as the distal opening in the sheath is inserted into a patient.

9. The guide device of claim 1, wherein the shield portion is formed at a distal end of the axial portion.

10. A method of insertion of a medical device comprising:
  inserting a guide device into a patient to a target location, the guide device including a mandrel, a sheath, and a blunt tipped shield portion near an end of the mandrel to protect a distal opening of the guide device while inserting the guide device;
  wherein inserting the guide device includes:
    inserting the mandrel with the blunt tipped shield portion near the end of the mandrel into the sheath;
    positioning the blunt tipped shield portion near a distal opening of the sheath; and
    inserting the sheath and mandrel with the blunt tipped shield portion into the patient.
  inserting a primary medical device into the guide device to the target location;
  removing the guide device from the patient without moving the primary medical device from the target location;
  wherein the guide device is radially removed from the primary medical device.

11. The method of claim 10, wherein the blunt tip tipped shield portion is solid.

12. The method of claim 10, wherein inserting the primary medical device into the guide device includes inserting the primary medical device into a continuous longitudinal guide region defined on a first longitudinal portion by the mandrel, and on a second longitudinal portion by the sheath.

13. The method of claim 12, wherein removing the guide device from the patient includes:
  removing the mandrel from the sheath wherein the first longitudinal portion of the longitudinal guide region is radially removed from a side of the primary medical device as it exits the patient; and
  removing the sheath from the patient by peeling the sheath apart radially from the side portion of the primary medical device as the sheath exits the patient.

14. The method of claim 12, wherein inserting the primary medical device into the substantially continuous longitudinal guide region includes inserting the primary medical device into one of a plurality of continuous longitudinal guide regions, each of the plurality of continuous guide regions being defined on a first longitudinal portion by the mandrel, and on a second longitudinal portion by the sheath.

15. The method of claim 12, wherein inserting the guide device includes;
  moving the primary medical device along the longitudinal guide region;
  engaging a ramp with the primary medical device; and
  directing the primary medical device radially from the mandrel with the ramp.

16. The method of claim 10, wherein inserting a guide device into a patient includes inserting the blunt tipped shield portion in a first shape during insertion of the guide device, and changing the blunt tipped shield portion to a second shape during removal of the guide device.

17. The method of claim 16, wherein changing the blunt tipped shield portion to a second shape during removal of the guide device includes deflating an inflatable chamber of the blunt tipped shield portion.

18. The method of claim 10, further comprising:
  positioning the blunt tipped shield portion defined by the mandrel near a distal tip of the sheath by adjusting a knob at a proximal end of the mandrel to engage a proximal end of the sheath;

after inserting the sheath and mandrel into the patient, moving the knob away from the sheath to allow access to a longitudinal guide region defined between the mandrel and the sheath;

wherein inserting a primary medical device includes inserting the primary medical device into the longitudinal guide region defined between the mandrel and the sheath and accessed only by moving the knob away from the proximal end of the sheath.

19. An insertion system comprising:

a guide device, having a guide axis, comprising:
- a sheath that defines a radially enclosed longitudinal cavity in a first state, and is adapted to be split substantially along a longitudinal wall and radially removed from the guide axis in a second state;
- a mandrel that, when inserted into the sheath in its first state, defines a substantially continuous longitudinal guide region bounded on a first longitudinal portion by the mandrel, and on a second longitudinal portion by the sheath;
- a primary medical device capable of insertion through the guide region;
- a shield portion, such that when the mandrel is fully inserted in the sheath, the shield portion substantially shields a distal opening in the sheath in its first state; and
- a ramp located near a distal end of the guide region between a proximal end of the mandrel and the shield portion, the ramp directing the distal end of the guide region at least partially radially outward from the guide axis.

20. The insertion system of claim 19, wherein the primary medical device includes an electrode.

21. The insertion system of claim 19, wherein the primary device includes a drug delivery device.

* * * * *

UNITED STATES PATENT AND TRADEMARK OFFICE
CERTIFICATE OF CORRECTION

PATENT NO.      : 7,588,581 B2                           Page 1 of 1
APPLICATION NO. : 10/106773
DATED           : September 15, 2009
INVENTOR(S)     : Solar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2296 days.

Signed and Sealed this

Twenty-first Day of September, 2010

David J. Kappos
*Director of the United States Patent and Trademark Office*